United States Patent [19]

Ishibe et al.

[11] 4,404,412

[45] Sep. 13, 1983

[54] TRICHLOROETHYLENE COMPOSITION STABILIZED AGAINST OXIDATION

[75] Inventors: Nobuyuki Ishibe; Jimmie K. Harden, both of Lake Jackson, Tex.

[73] Assignee: The Dow Chemical Company, Midland, Mich.

[21] Appl. No.: 345,874

[22] Filed: Feb. 4, 1982

[51] Int. Cl.$^3$ ............................................. C07C 17/42
[52] U.S. Cl. ..................................... 570/109; 570/112; 570/106; 570/117; 570/120
[58] Field of Search ................. 570/109, 112; 252/401, 252/405, 394

[56] References Cited

U.S. PATENT DOCUMENTS 3,564,063  2/1971  Cormany et al. .................... 570/112

3,959,397  5/1976  Richtzenhain et al. ............. 570/112

FOREIGN PATENT DOCUMENTS 664073  5/1963  Canada ................................. 570/112
430671  2/1967  Switzerland ........................ 570/109
502838  3/1939  United Kingdom ................ 252/405
548592  3/1977  U.S.S.R. .............................. 570/112

*Primary Examiner*—Charles F. Warren
*Assistant Examiner*—Joseph A. Boska
*Attorney, Agent, or Firm*—A. C. Ancona

[57] ABSTRACT

Trichloroethylene is stabilized against oxidation by adding a nitrogen-containing compound selected from among α-(dimethylamino) propionitrile, thiazole, 1-aza-2-alkoxy-1-cycloalkene and 1,5-diazabicyclo[5.4.0]undec-5-ene. These may be used in combination with ethyl acetate, acetonitrile and pyrazine.

4 Claims, No Drawings

TRICHLOROETHYLENE COMPOSITION STABILIZED AGAINST OXIDATION

BACKGROUND OF THE INVENTION

Numerous solvents have been employed in degreasing operations. Among these, solvents of the chlorinated hydrocarbon type, including both saturated compounds such as carbon tetrachloride, and unsaturated compounds such as trichloroethylene and perchloroethylene, have been widely employed because of their high grease-solvent capacity and low flammability. Trichloroethylene is probably most widely used in degreasing. However, it is seldom used without the addition of some "stabilizer," adapted to prevent or retard its decomposition during storage and normal use. This socalled "normal" type of decomposition is promoted by light and oxygen. The action of light and oxygen is accelerated by heat. Several stabilizers are available and commonly used for the purpose of inhibiting this decomposition.

Numerous variations of the degreasing operation have been employed. In one method, the metal article to be degreased is brought into contact with the solvent in the liquid phase. This is accomplished by immersing the article in a large body of the solvent, or by spraying the solvent on the surface of the article. In another common method of degreasing, known generally as vapor-phase degreasing, a body of solvent is maintained at the boiling point and in communication with a chamber adapted to contain a large body of the solvent vapor. The article to be degreased is brought into contact with this body of vapor, and causes condensation of the solvent on the greasy metal surface. The condensed solvent removes grease and oil from the metal surface and drips off, usually returning to the boiling body of the solvent. With it goes dirt, adhering to the greasy surface, which often includes metal chips.

Pyrrole and N-alkyl pyrroles, especially those in which the alkyl group contains 1 to 4 carbon atoms, are the preferred stabilizers for trichloroethylene. Examples of these are pyrrole, N-methyl pyrrole, N-ethyl pyrrole, 2-methyl pyrrole, 3-methyl pyrrole, 2,4-dimethyl pyrrole, 2,5-dimethyl pyrrole, N-propyl pyrrole and 2-chloropyrrole. The use of these stabilizers was first disclosed in U.S. Pat. No. 2,492,048. Another well-known inhibitor or stabilizer for trichloroethylene or perchloroethylene when used as a degreasing solvent is a group of organic esters. Specific examples include ethyl acetate, isopropyl acetate, butyl hexanoate, amyl acetate, n-butyl formate and the like. The above are disclosed as useful for stabilizers in U.S. Pat. No. 2,371,647.

A combination stabilizer is disclosed in U.S. Pat. No. 2,818,446 wherein esters such as the above are combined with an epoxide such as propylene oxide, butylene oxide or epichlorohydrin. Ethyl acetate and epichlorohydrin is a preferred combination.

Epoxides are also used in combination with amines as disclosed in U.S. Pat. No. 2,797,250. Amines both aliphatic, such as triethylamine, and aromatic, such as pyridine and the picolines, are useful in combination with epoxides such as butylene oxide or epichlorohydrin.

Another combination stabilizer, described in U.S. Pat. No. 2,906,783, consists of an epoxide, an ester, an alkene hydrocarbon and an azine. For example, trichloroethylene was stabilized by the addition of butylene oxide, isopropyl acetate, trimethylpentane and acetalazine. Other useful azines are derivatives of aliphatic aldehydes, e.g. propionaldehyde azine or butyraldehyde azine. Pyrazine and nitriles have been used to stabilize methylchloroform as disclosed in U.S. Pat. Nos. 3,798,170 and 3,564,063, respectively. Various other combinations, e.g. propargyl alcohol and pyrrole (U.S. Pat. No. 2,803,676); an amine borane, alkyl borane or an ammonium salt of borane (U.S. Pat. No. 2,917,555); organic tri-substituted amines wherein at least one substituent group is unsaturated (U.S. Pat. No. 2,997,507); and thioethers and thioalcohols (U.S. Pat. No. 2,998,462) also have been employed as stabilizers.

It has now been discovered that certain nitrogen-containing compounds, not hitherto disclosed, are useful as stabilizers against oxidation of trichloroethylene when exposed to light and heat. They are:

(1) α-(dimethylamino) propionitrile,

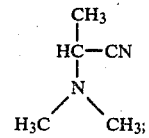

and certain cyclic compounds; (2) thiazole,

(3) 1-aza-2-alkoxy-1-cycloalkene, having the formula

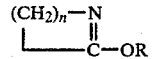

wherein R is an alkyl radical having 1 to 4 carbon atoms and n is an integer of from 1 to 5; and (4) 1,5-diazabicyclo[5.4.0]undec-5-ene,

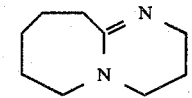

SUMMARY OF THE INVENTION

Certain nitrogen-containing compounds have been found useful as stabilizers against oxidation when added to trichloroethylene. These are α-(dimethylamino) propionitrile, thiazole, 1-aza-2-alkoxy-1-cycloalkenes and 1,5-diazabicyclo[5.4.0]undec-5-ene.

DETAILED DESCRIPTION OF THE INVENTION

Other nitrogen-containing compounds have been found to be oxidation inhibitors to replace inhibitors such as N-methyl pyrrole now employed to stabilize trichloroethylene against oxidation. These compounds were tested and compared with the effectiveness of N-methyl pyrrole, butylene oxide, ethyl acetate, acetonitrile and pyrazine, each known as stabilizers for certain of the chlorinated solvents. Some of these were also found to be effective in combination with the compounds of the invention.

The following description is of the tests employed to show the effectiveness of the invention.

Accelerated Oxidation Test

Oxygen was slowly bubbled into a trichloroethylene solution (50 ml) containing 5% water in the presence of a steel coupon at 80° C. for 24 hours. Corrosion of the metal was examined. The reaction mixture was added to 100 ml of methanol containing a bromothymol blue indicator. The solution was titrated with 0.1 N NaOH to determine the extent of acid formation. The results for those chemicals screened are summarized in Table I.

Seven-Day Reflux in the Presence of Various Metals

An unfractionated (U) or fractionated (top, T, or bottom, B) solution with equal volume is refluxed for seven days in dry or wet (7% water added) condition in the presence of metals including Al-1100, 2024, 7074, Zn, Cu, Ni, steel, stainless steel, brass and monel. Corrosion of metals and discoloration of solutions are visually judged. Relative ratings are given wherein five is the worst and zero the best. The results are given in Table II.

TABLE I

| | | Acid Content | |
|---|---|---|---|
| Antioxidant (wt. %) | Additive (wt. %) | Before ppm | After ppm |
| Control | (no stabilizers) | 9.8 | 173 |
| — | Butylene oxide (0.2–0.5) | 5.7 | 12.2 |
| — | Ethyl acetate (0.1–0.5) | 7.7 | 58.1 |
| — | Acetonitrile (0.25) | 7.7 | 27.2 |
| — | Pyrazine (0.1–0.5) | 10.2 | 120 |
| 1,5-Diazabicyclo-[5.4.0]undec-5-ene (0.02) | — | 5.0 | 5.3 |
| 1,5-Diazabicyclo-[5.4.0]undec-5-ene (0.02) | Pyrazine (0.25) | 0 | 0 |
| 1,5-Diazabicyclo-[5.4.0]undec-5-ene (0.02) | Ethyl acetate (0.25) | 5.6 | 5.6 |
| α-Dimethylamino-propionitrile (0.02) | — | 10.0 | 12.3 |
| α-Dimethylamino-propionitrile (0.02) | Ethyl acetate (0.25) | 9.2 | 11.8 |
| α-Dimethylamino-propionitrile (0.02) | Pyrazine (0.25) | 3.8 | 11.3 |
| α-Dimethylamino-propionitrile (0.02) | Acetonitrile (0.25) | 6.5 | 6.5 |
| 1-Aza-2-methoxy-1-cycloheptene (0.02) | — | 7.4 | 9.7 |
| Thiazole | — | 15.0 | 15.3 |
| N—methylpyrrole (0.02) | — | 10.0 | 10.2 |
| N—methylpyrrole (0.02) | Ethyl acetate (0.25–0.5) | 9.0 | 9.7 |
| N—methylpyrrole (0.02) | Pyrazine (0.10–0.50) | 9.8 | 10.1 |
| N—methylpyrrole (0.02) | Acetonitrile (0.10–0.50) | 9.4 | 13.0 |

Butylene oxide, ethyl acetate, acetonitrile, or pyrazine cannot inhibit oxidative degradation of trichloroethylene in the absence of an antioxidant. Addition of 1,5-diaza[5.4.0]undec-5-ene, α-(dimethylamino)propionitrile, 1-aza-2-methoxy-1-cycloheptene, or thiazole can prevent the acid formation as effectively as N-methylpyrrole.

The antioxidant nitrogen-containing compounds of the invention are usefully employed in trichloroethylene when used in concentrations within the range of from about 0.01 to about 0.5% by weight based on the trichloroethylene. A preferred range is from about 0.02 to about 0.2%.

When used in combination with other known stabilizers, the other stabilizers are present in amounts of from about 0.1% to about 0.5% by weight and preferably from about 0.2% to about 0.3% by weight.

TABLE II

| | | Rating | | | | | |
|---|---|---|---|---|---|---|---|
| | | U Unfract. | | T Fract. Top | | B Fract. Bottom | |
| Formulation (Wt. %) | Metal | Dry | Wet | Dry | Wet | Dry | Wet |
| Thiazole (0.1) | Al-1100 | 0 | 0 | 0 | 0 | 0 | 0 |
| | Cu | | | | | | |
| | Ni | | | | | | |
| | SS* | | | | | | |
| | brass | | | | | | |
| | Monel | | | | | | |
| | Al-2024 | 0 | 2 | 0 | 3 | 0 | 2 |
| | Al-7075 | 0 | 0 | 0 | 3 | 0 | 2 |
| | Steel | 0 | 2 | 0 | 3 | 0 | 2 |
| | Zn | 0 | 2 | 0 | 0 | 0 | 0 |
| Pyrazine (0.25) + 1,5-Diazabicyclo[5.4.0]-undec-5-ene (0.02) | Al-1100 | 0 | 3 | 0 | 2 | 0 | 1 |
| | Al-2024 | | | | | | |
| | Al-7075 | 0 | 1 | 0 | 1 | 0 | 1 |
| | brass | | | | | | |
| | Zn | | | | | | |
| | Monel | | | | | | |
| | SS | | | | | | |
| | Ni | | | | | | |
| | Steel | 0 | 3 | 0 | 3 | 0 | 1 |
| Acetonitrile (0.25) + α-(Dimethylamino)-propionitrile (0.02) | Al-1100 | 0 | 0 | — | — | — | — |
| | Al-2024 | | | | | | |
| | Al-7075 | | | | | | |
| | brass | | | | | | |
| | Monel | | | | | | |
| | SS | | | | | | |
| | Ni | | | | | | |
| | Cu | 2 | 2 | — | — | — | — |
| | Zn | 0 | 2 | — | — | — | — |
| | Steel | 0 | 4 | — | — | — | — |

*SS = stainless steel

From the data in the above two tables one can see that the nitrogen-containing compounds of the invention are antioxidants in their own right, but that when combined with certain known inhibitors—not antioxidants—the degradation and corrosion inhibition are improved.

Thus, the invention disclosed herein is the use of an organic nitrogen-containing compound which is an antioxidant, alone or in combination with known stabilizers, in trichloroethylene to stabilize it against oxidation and degradation promoted by light and heat. These compounds are α-(dimethylamino)propionitrile, thiazole, 1,5-diazabicyclo-[5.4.0]undec-5-ene and a 1-aza-2-alkoxy-1-cycloalkene wherein the alkoxy group contains 1 to 4 carbon atoms and the cyclic ring contains from 3 to 7 carbon atoms.

We claim:

1. A stable chlorinated solvent useful in degreasing operations which comprises trichloroethylene and a minor amount of a stabilizer which is an antioxidant consisting of α, 1,5-diazabicyclo-[5.4.0]undec-5-ene.

2. The product of claim 1 wherein the antioxidant compound is employed in a concentration of from about 0.01% to about 0.5% by weight based on the trichloroethylene.

3. The product of claim 2 wherein the stabilizing antioxidant compound is employed in combination with pyrazine.

4. The product of claim 3 wherein the pyrazine, is present in a concentration of from about 0.1% to about 0.5% by weight based on the trichloroethylene.

* * * * *